(12) United States Patent
Ju et al.

(10) Patent No.: US 10,357,665 B2
(45) Date of Patent: Jul. 23, 2019

(54) RADIATION THERAPY APPARATUS AND QUALITY CONTROL METHOD FOR RADIATION THERAPY APPARATUS

(71) Applicant: Samsung Life Public Welfare Foundation, Seoul (KR)

(72) Inventors: Sang Gyu Ju, Seoul (KR); Chae Seon Hong, Gyeonggi-do (KR); Doo Ho Choi, Seoul (KR)

(73) Assignee: Samsung Life Public Welfare Foundation, Seoul (KR)

( * ) Notice: Subject to any disclaimer, the term of this patent is extended or adjusted under 35 U.S.C. 154(b) by 310 days.

(21) Appl. No.: 15/513,701

(22) PCT Filed: Nov. 10, 2015

(86) PCT No.: PCT/KR2015/012044
§ 371 (c)(1),
(2) Date: Mar. 23, 2017

(87) PCT Pub. No.: WO2016/076598
PCT Pub. Date: May 19, 2016

(65) Prior Publication Data
US 2017/0291043 A1    Oct. 12, 2017

(30) Foreign Application Priority Data

Nov. 10, 2014  (KR) ........................ 10-2014-0155516

(51) Int. Cl.
*A61N 5/10*     (2006.01)
*A61B 6/00*     (2006.01)
*A61B 6/08*     (2006.01)

(52) U.S. Cl.
CPC ............ *A61N 5/1075* (2013.01); *A61B 6/587* (2013.01); *A61N 5/10* (2013.01); *A61N 5/1048* (2013.01);
(Continued)

(58) Field of Classification Search
CPC .............................. A61N 5/10; A61N 2005/10
See application file for complete search history.

(56) References Cited

U.S. PATENT DOCUMENTS 6,553,091 B2 *  4/2003  Takanashi ............. A61B 6/035
378/15
7,559,693 B2    7/2009  Sonani
(Continued)

FOREIGN PATENT DOCUMENTS

CN    102138803 A    8/2011
CN    103736211 A    4/2014
(Continued)

OTHER PUBLICATIONS

International Search Report and Written Opinion issued by the Korean Intellectual Property Office, acting as the ISA, for International Application PCT/KR2015/012044 dated Mar. 16, 2016.
(Continued)

*Primary Examiner* — Thomas R Artman
(74) *Attorney, Agent, or Firm* — McCarter & English, LLP

(57) ABSTRACT

Provided is a radiation therapy apparatus on which quality management is performed. The radiation therapy apparatus includes: a body unit; a gantry coupled to one side of the body unit and formed to be rotatable in at least one direction with regard to the body unit; a radiation irradiating head formed at one side of the gantry to irradiate a radiation; and a level control module formed at one side of the radiation irradiating head to measure a rotation angle of the gantry or the radiation irradiating head, compare the measured rotation angle with a rotation angle indicated by an angle indicator of the radiation therapy apparatus, and correct an error of the angle indicator.

14 Claims, 4 Drawing Sheets

(52) U.S. Cl.
CPC ......... *A61B 6/08* (2013.01); *A61N 2005/1074* (2013.01)

(56) References Cited

U.S. PATENT DOCUMENTS

| | | | |
|---|---|---|---|
| 7,755,031 B2 | 7/2010 | Jang et al. | |
| 8,022,374 B2 | 9/2011 | Seo et al. | |
| 8,360,639 B2 | 1/2013 | Kato | |
| 9,628,723 B2* | 4/2017 | Yu | A61B 6/032 |
| 2001/0055362 A1* | 12/2001 | Takanashi | A61B 6/035 378/15 |
| 2007/0197908 A1 | 8/2007 | Ruchala et al. | |
| 2011/0103556 A1 | 5/2011 | Carn | |
| 2012/0209555 A1* | 8/2012 | Tang | A61B 6/032 702/104 |
| 2016/0166228 A1* | 6/2016 | Li | G05B 19/416 700/275 |
| 2016/0239971 A1* | 8/2016 | Yu | A61B 6/032 |
| 2017/0291043 A1* | 10/2017 | Ju | A61N 5/10 |

FOREIGN PATENT DOCUMENTS

| | | |
|---|---|---|
| KR | 20-0222503 Y1 | 5/2001 |
| KR | 20-0427116 Y1 | 9/2006 |
| KR | 10-2008-0039920 A | 5/2008 |
| KR | 10-2009-0081883 A | 7/2009 |
| WO | WO 92/00657 A1 | 1/1992 |
| WO | WO 01/60236 A2 | 8/2001 |
| WO | WO 2007/014104 A2 | 2/2007 |

OTHER PUBLICATIONS

Office action issued by the Korean Intellectual Property Office for priority application KR 10-2014-0155516 dated Nov. 15, 2016.

* cited by examiner

RADIATION THERAPY APPARATUS AND QUALITY CONTROL METHOD FOR RADIATION THERAPY APPARATUS

CROSS-REFERENCE TO RELATED APPLICATIONS

This application is the National Stage entry under 35 U.S.C. § 371 of International Application Number PCT/KR2015/012044 filed on Nov. 10, 2015, published on May 19, 2016 under publication number WO 2016/076598 A1, which claims the benefit of priority under 35 U.S.C. § 119 of Korean patent application number 10-2014-0155516 filed Nov. 10, 2014.

TECHNICAL FIELD

Embodiments of the inventive concept relate to a radiation therapy apparatus and a quality management method for a radiation therapy apparatus, and more particularly, to a radiation therapy apparatus and a quality management method for a radiation therapy apparatus that may automatically measure the accuracy of a rotation speed and an angle indicator value of a gantry or a radiation irradiating head and may correct the same.

BACKGROUND ART

Radiation therapy is a method of delaying or preventing the growth of a malignant tissue or extinguishing the malignant tissue by damaging or destroying a target tissue by using high-energy waves such as X-rays or gamma-rays or high-energy particles such as electron beams or proton beams. Recently, a radiation surgery method for treating without incision surgery by irradiating a large amount of radiation at one time has also been developed to replace a neurosurgical surgery method incising a skull.

It has recently been generalized such that about 60% or more of cancer patients may receive radiation therapy. Not only being used to treat a tumor by itself, radiation therapy may be used to reduce the size of a tumor to facilitate a surgical surgery or to destroy a malignant cell left after surgery, by being used together with other surgical surgeries for treating a local portion that fails to be removed by surgery or where surgery is difficult because a tumor is large and invasive.

Extracorporeal radiation therapy apparatuses for irradiating radiations from outside may be classified into low-energy X-ray therapy apparatuses, radioisotope therapy apparatuses, linear accelerators, particle accelerators, and the like according to the methods of generating high-energy particles or radiations.

The low-energy X-ray therapy apparatuses have been used to treat skin diseases or deep portions by using X-ray generating apparatuses, but they are rarely used nowadays.

The radioisotope therapy apparatuses use gamma-rays generated from radioisotopes such as cobalt-60 (Co-60). The radioisotope therapy apparatuses use gamma-rays having somewhat higher energy than the X-rays of the low-energy X-ray therapy apparatuses, but their use is gradually decreasing.

As apparatuses used as the standard of radiation therapy, the linear accelerators may output X-rays and electron beams, may transmit various energy, and may provide a high dose rate and beam-forming.

The particle accelerators have a structure for transferring neutron or proton particles accelerated by a cyclotron accelerator through a beam transfer pipe and emitting the same to a desired region through a nozzle, and may minimize a dose at a normal tissue and concentrate energy only on a deep tumor because they have a deeper Bragg's peak than the linear accelerators.

Recent medical radiation therapy apparatuses are developed in the form of mounting a radiation emitting head on a gantry having an arm or in the form of having a ring-type gantry, and a structure in which a radiation emitting head and a radiation detector face each other with a human body therebetween and rotate around the human body is mainly used. Information disclosed in this Background section was already known to the inventors before achieving the inventive concept or is technical information acquired in the process of achieving the inventive concept. Therefore, it may contain information that does not form the prior art that is already known to the public in this country.

DETAILED DESCRIPTION OF THE INVENTION

Technical Problem

Embodiments of the inventive concept are to provide a radiation therapy apparatus and a quality management method for a radiation therapy apparatus that may automatically measure the accuracy of a rotation speed and an angle indicator value of a gantry or a radiation irradiating head and may correct the same.

Technical Solution

According to an embodiment of the inventive concept, a radiation therapy apparatus on which quality management is performed includes: a body unit; a gantry coupled to one side of the body unit and formed to be rotatable in at least one direction with regard to the body unit; a radiation irradiating head formed at one side of the gantry to irradiate a radiation; and a level control module formed at one side of the radiation irradiating head to measure a rotation angle of the gantry or the radiation irradiating head, compare the measured rotation angle with a rotation angle indicated by an angle indicator of the radiation therapy apparatus, and correct an error of the angle indicator.

Herein, the level control module may include: one or more electronic level meters measuring a rotation angle of the gantry or the radiation irradiating head; and a control unit comparing the rotation angle of the gantry or the radiation irradiating head measured by the electronic level meter with a rotation angle indicated by an angle indicator of the radiation therapy apparatus and correcting an error of the angle indicator.

Herein, the radiation therapy apparatus may further include a level adjuster formed on at least one side of the electronic level meter to move the electronic level meter in at least one direction and correct a level error of the electronic level meter.

Herein, the control unit may notify an error occurrence to a user when the error of the angle indicator is greater than or equal to a predetermined allowable error.

Herein, a module mounting guide may be formed at one side of the radiation irradiating head, and the level control module may be mounted on the module mounting guide.

Herein, the radiation therapy apparatus may further include a report generating unit generating and providing a result report of the quality management executed by the level control module.

Herein, the radiation therapy apparatus may further include a control module calculates a rotation speed of the gantry or the radiation irradiating head and angle information of the gantry or the radiation irradiating head at a particular time by using measurement time information and the rotation angle of the gantry or the radiation irradiating head measured by the level control module, and compares the calculated rotation speed and an angle of the gantry or the radiation irradiating head at a particular time with a rotation speed of the gantry or the radiation irradiating head predetermined at the time of radiation therapy planning and an angle of the gantry or the radiation irradiating head at a particular time.

Herein, the control module may generate a predetermined alarm signal when a difference between the calculated rotation speed and the angle of the gantry or the radiation irradiating head at a particular time and the rotation speed of the gantry or the radiation irradiating head predetermined at the time of radiation therapy planning and the angle of the gantry or the radiation irradiating head at a particular time exceeds a predetermined error range.

According to another embodiment of the inventive concept, a quality management method for a radiation therapy apparatus includes: mounting a level control module on the radiation therapy apparatus; moving a gantry to an initial position; measuring a rotation angle of the gantry or a radiation irradiating head at each position by using an electronic level meter while moving the gantry or the radiation irradiating head to one or more positions; and comparing the measured rotation angle with a rotation angle indicated by an angle indicator of the radiation therapy apparatus and correcting an error of the angle indicator.

Herein, the quality management method may further include correcting an error of the electronic level meter by a level adjuster formed on at least one side of the electronic level meter to move the electronic level meter in at least one direction.

Herein, the quality management method may further include resetting the level control module after the moving of the gantry to the initial position.

Herein, by comparing the measured rotation angle with the rotation angle indicated by the angle indicator of the radiation therapy apparatus, an error occurrence may be notified to a user when the error of the angle indicator is greater than or equal to a predetermined allowable error.

Herein, the quality management method may further include, after correcting of the error of the angle indicator, generating and providing a result report of the quality management executed by the level control module.

These and/or other aspects will become apparent and more readily appreciated from the following description of the invention, taken in conjunction with the accompanying drawings.

Advantageous Effects of the Invention

By the radiation therapy apparatus and the quality management method for the radiation therapy apparatus according to the embodiments of the inventive concept, it is possible to calculate an error or the angle indicator and correct the same. Accordingly, accurate/precise quality management may be performed on the angle indicator.

Also, by using the automated angle correcting device, automated quality management may be performed, and the time, cost, and manpower required for quality management may be reduced.

Also, since the quality management results of the respective quality management items performed may be analyzed and the result report thereof may be automatically generated and stored, the quality management history thereof may be systematically stored and analyzed.

BEST MODE

Figure 1:
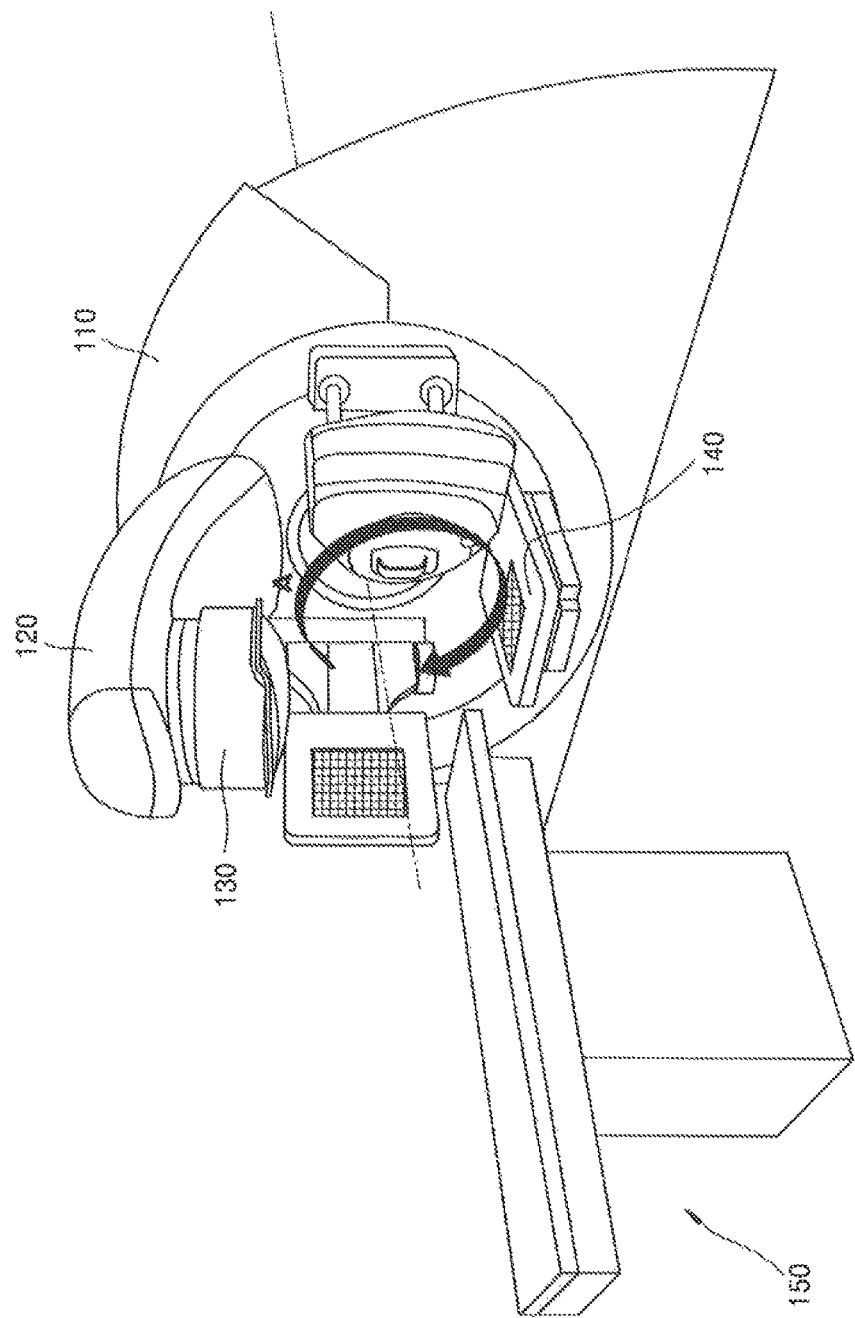
FIG. 1 is a diagram illustrating a radiation therapy apparatus according to an embodiment of the inventive concept.

The inventive concept may include various embodiments and modifications, and certain embodiments thereof are illustrated in the drawings and will be described herein in detail. The effects and features of the inventive concept and the accomplishing methods thereof will become apparent from the following description of the embodiments, taken in conjunction with the accompanying drawings. However, the inventive concept is not limited to the embodiments described below, and may be embodied in various modes. It will be understood that although the terms "first", "second", etc. may be used herein to describe various components, these components should not be limited by these terms. These terms are only used to distinguish one component from another. Also, as used herein, the singular forms "a", "an", and "the" are intended to include the plural forms as well, unless the context clearly indicates otherwise. Also, it will be understood that the terms "comprise", "include" and "have" used herein specify the presence of stated features or components, but do not preclude the presence or addition of one or more other features or components. Also, the sizes of components in the drawings may be exaggerated for convenience of description. In other words, since the sizes and thicknesses of components in the drawings are arbitrarily illustrated for convenience of description, the following embodiments are not limited thereto.

Hereinafter, embodiments of the inventive concept will be described in detail with reference to the accompanying drawings. In the following description, like reference numerals will denote like elements, and redundant descriptions thereof will be omitted.

Figure 2:
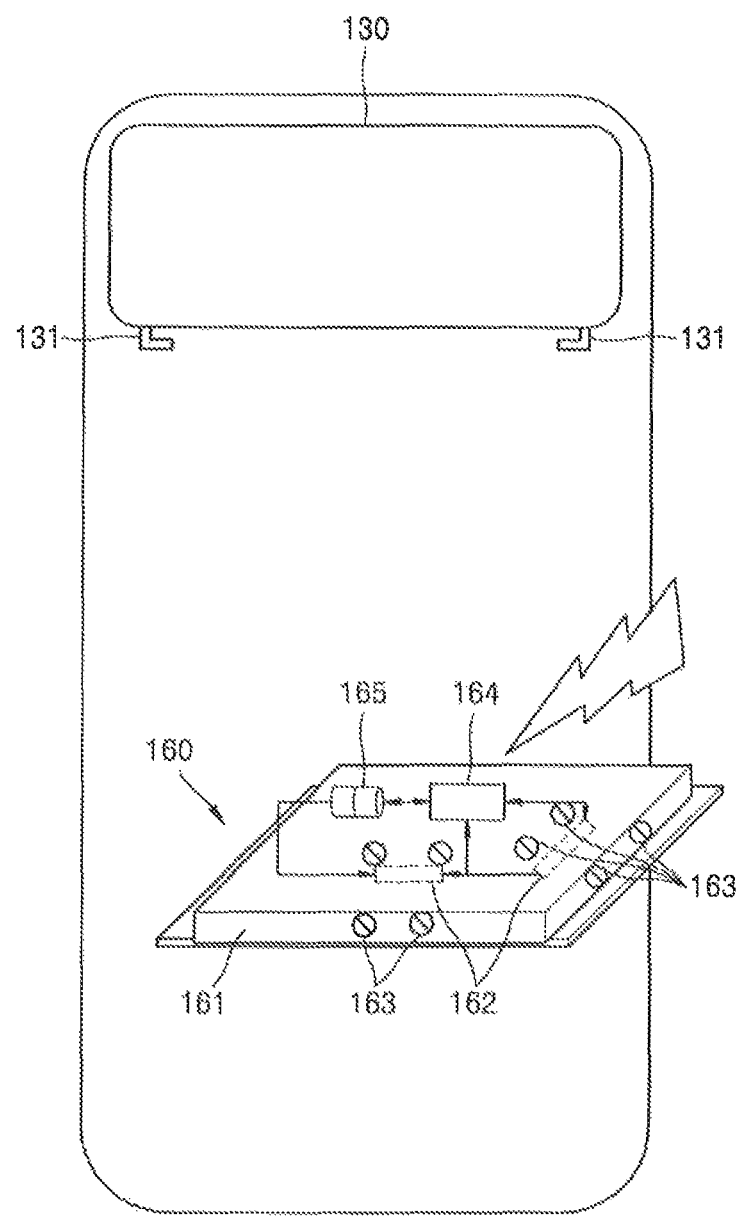
FIG. 2 is a conceptual diagram schematically illustrating the radiation therapy apparatus of FIG. 1.
Figure 3:
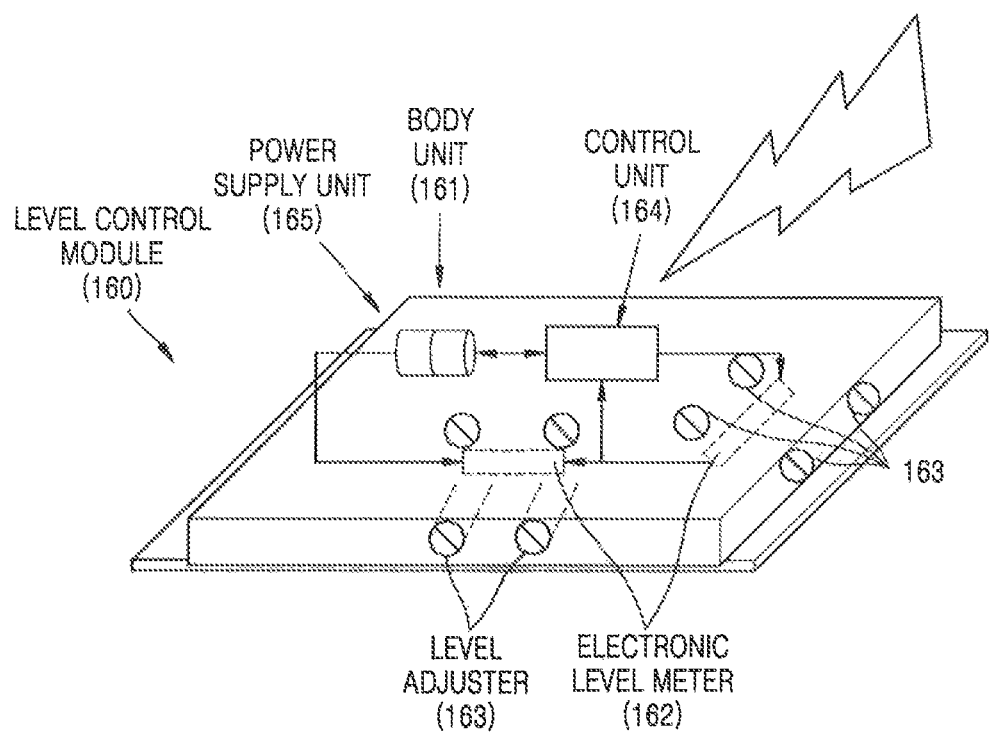
FIG. 3 is an enlarged view of a level control module of FIG. 2.

FIG. 1 is a diagram illustrating a radiation therapy apparatus according to an embodiment of the inventive concept, FIG. 2 is a conceptual diagram schematically illustrating the radiation therapy apparatus of FIG. 1, and FIG. 3 is an enlarged view of a level control module of FIG. 2.

Referring to FIGS. 1, 2, and 3, a radiation therapy apparatus 100 according to an embodiment of the inventive concept may include a body unit 110, a gantry 120, a radiation irradiating head 130, an image acquiring unit 140, a bed unit 150, and a level control module 160. This will be described below in more detail.

Radiation therapy is a therapy method for treating a cancer by irradiating a high-dose radiation intensively to a tumor. Successful radiation therapy requires a therapy technology for concentrating a radiation on a tumor while minimizing the damage to surrounding normal organs, an accurate radiation therapy apparatus, and various image or dose detecting apparatuses.

Recently, with the widespread use of high-accuracy radiation therapy apparatuses, high-dose irradiation using high-level therapy technology has been generalized. The high-dose irradiation has improved the tumor removal efficiency, but the potential risk of radiation accidents due to erroneous irradiation has also increased. Thus, recently, in order to prevent these radiation accidents, the strict quality management (quality assurance) of therapy apparatuses has been prescribed by law.

Meanwhile, rotation of a gantry and a radiation irradiating head (collimator) is necessary to accurately irradiate a radiation to a tumor by using a radiation therapy apparatus. In this case, for accurate radiation irradiation, it is necessary to determine whether a value of an angle indicator mounted on the therapy apparatus is accurate, and for this purpose, a manager periodically performs quality management by using a protractor. In the conventional method, since quality management is based on the subjective judgment of a tester, it is inaccurate and time-consuming and particularly its automation is impossible.

In order to solve these problems, by including the level control module 160 including an electronic level meter and a level adjuster, the radiation therapy apparatus 100 according to an embodiment of the inventive concept measures the angles of the gantry 120 and the radiation irradiating head 130 at various angles, compares an angle measured by the level control module 160 with a rotation angle indicated by an angle indicator (not illustrated), automatically measures a rotation error, and corrects the same. This will be described below in more detail.

Referring to FIG. 1, the body unit 110 forms a base unit of the radiation therapy apparatus 100 and becomes a standard for rotation of the gantry 120, the radiation irradiating head 130, and the image acquiring unit 140.

The gantry 120 may be coupled to one side of the body unit 110 and formed to be rotatable in at least one direction with respect to the body unit 110. In this case, the image acquiring unit 140 formed to face the radiation irradiating head 130 of the gantry 120 may rotate together with the gantry 120. That is, the gantry 120, the radiation irradiating head 130, and the image acquiring unit 140 may be formed to be rotatable in the direction of an arrow A in FIG. 1 (or in the opposite direction thereof).

The radiation irradiating head 130 may be formed at one side of the gantry 120 to irradiate a radiation. Herein, the radiation irradiating head 130 may emit X-rays, gamma-rays, high-energy electron beams, high-energy proton beams, or other high-energy particle beams.

Also, the radiation irradiating head 130 may include any one of an X-ray generating apparatus, a radioisotope source, and a linear accelerator. Alternatively, the radiation irradiating head 130 may receive and emit high-energy particle beams accelerated and generated by a particle accelerator installed outside the radiation therapy apparatus. Alternatively, the radiation irradiating head 130 may include a multi-leaf collimator (MLC). By using the multi-leaf collimator, the radiation irradiating head 130 may provide internal beamforming, thus enabling more efficient radiation energy transmission.

Meanwhile, a module mounting guide 131 may be formed to protrude in the direction of irradiation of a radiation from the radiation irradiating head 130, and the level control module 160 may be coupled to the module mounting guide 131.

The image acquiring unit 140 may include an image sensor or a detector sensor and may detect a radiation and convert the same into an electrical signal to acquire an image. An electronic portal imaging device (EPID) may be used as an embodiment of the image acquiring unit 140. In detail, in the radiation therapy using high-energy radiation, in order to detect the position of a diseased part of a patient, the EPID technology may detect the radiation transmitted through the patient and convert the same into an electrical signal to acquire an image or dose distribution. That is, the image acquiring unit 140 may acquire a radiation image or may acquire a dose distribution.

The image acquiring unit 140 may be mounted on any one of the body unit 110, the gantry 120, and the radiation irradiating head 130. Alternatively, the image acquiring unit 140 may be independently mounted on the bed unit 150 without being mounted on the radiation therapy apparatus, or may be installed by using a separate support.

The bed unit 150 may be formed such that the patient may lie thereon, and may be configured to move in an X-axis direction, a Y-axis direction, or a Z-axis direction with respect to the radiation irradiated from the radiation irradiating head 130.

The level control module 160 may measure a rotation angle of the gantry 120 or the radiation irradiating head 130, compare the measured rotation angle with a rotation angle indicated by an angle indicator (not illustrated) of the radiation therapy apparatus 100, and automatically correct an error of the angle indicator. The level control module 160 may include a body unit 161, an electronic level meter 162, a level adjuster 163, a control unit 164, and a power supply unit 165.

The body unit 161 may form a base unit of the level control module 160, and both end portions of the body unit 151 may be formed in the shape of a step such that it may be mounted on the module mounting guide 131 of the radiation irradiating head 130.

One or more electronic level meters 162 may be formed on the body unit 161 and may measure the rotation angle of the gantry 120 or the radiation irradiating head 130.

The level adjuster 163 may be formed on at least one side of the electronic level meter 162 and may correct a level error of the electronic level meter 162. The level adjuster 163 may include, for example, a motor or an actuator and may be formed on at least one side of the electronic level meter 162 to move the electronic level meter 162 with respect to an X axis, a Y axis, or a Z axis.

The control unit 164 may compare the rotation angle of the gantry 120 or the radiation irradiating head 130 measured by the electronic level meter 162 with a rotation angle indicated by an angle indicator (not illustrated) of the radiation therapy apparatus 100 and automatically correct an error of the angle indicator. Although the control unit 164 is illustrated as being formed in the level control module 160, the inventive concept is not limited thereto and the control unit 164 may be formed in a separate quality management server. In this case, wired/wireless communication may be performed between the level control module 160 and a quality management server (not illustrated) to transmit/receive data such as the rotation angle of the gantry 120 or the radiation irradiating head 130 measured by the electronic level meter 162.

Also, the control unit 164 may control the level adjuster 163 to correct a level error of the electronic level meter 162.

The power supply unit 165 may supply the power necessary to drive the electronic level meter 162, the level adjuster 163, and the control unit 164.

Although not illustrated, the level control module 160 may further include a report generating unit (not illustrated). The report generating unit (not illustrated) may analyze the result of the quality management performed by the level control module 160 and generate a result report thereof. That is, the report generating unit may automatically analyze the quality management performance result and provide the same to a user.

According to the inventive concept described above, since an error of the angle indicator may be calculated and corrected, accurate/precise quality management may be performed on the angle indicator. Also, by using the automated angle correcting device, automated quality management may be performed, and the time, cost, and manpower required for quality management may be reduced. Also, since the quality management results of the respective quality management items performed may be analyzed and the result report thereof may be automatically generated and stored, the quality management history thereof may be systematically stored and analyzed.

Although not illustrated, the radiation therapy apparatus 100 according to an embodiment of the inventive concept may further include a control module (not illustrated).

In detail, intensity-modulated arc therapy or volumetric arc therapy, which irradiates radiation while rotating in order to concentrate a radiation dose distribution on a tumor and reduce a surrounding normal organ dose, has recently been spotlighted. In the volumetric arc therapy, the gantry 120 is rotated to irradiate a radiation according to the shape of a tumor at each corresponding angle to maximize a possible dose at the tumor, and it is important to accurately irradiate a predetermined radiation dose at a predetermined angle.

For this purpose, it is necessary to accurately control the radiation irradiation angle and the rotation speed of the gantry 120 of the radiation therapy apparatus 100. For this purpose, the control module (not illustrated) of the radiation therapy apparatus 100 according to an embodiment of the inventive concept may continuously acquire the rotation angle of the gantry 120 or the radiation irradiating head 130 and the corresponding time information from the electronic level meter 162 attached to the gantry 120, calculate the rotation speed thereof based on this, compare the calculated rotation speed with the gantry rotation speed designed in therapy planning, automatically generate an alarm in the event of an error, and generate a trigger signal for stopping the therapy apparatus. Also, in order to perform this function more objectively, the control module (not illustrated) may set an allowable error range and automatically generate an alarm when the allowable error range is exceeded.

Also, the control module (not illustrated) may measure the rotation speed of the gantry 120 or the radiation irradiating head 130 and the rotation angle at the radiation irradiation time, acquire a log file of information related to the radiation irradiation such as a monitor unit and a multi-leaf collimator shape at this time from the apparatus, and compare the same with the corresponding value planned through a therapy planning device to determine whether there is an error.

According to the inventive concept described above, when radiation therapy is performed simultaneously with gantry rotation as in the intensity-modulated arc therapy, since quality management is performed against improper irradiation due to the rotation speed or the corresponding angle recognition error, a radiation irradiation error may be prevented and an accurate therapy may be implemented.

MODE OF THE INVENTION

Figure 4:
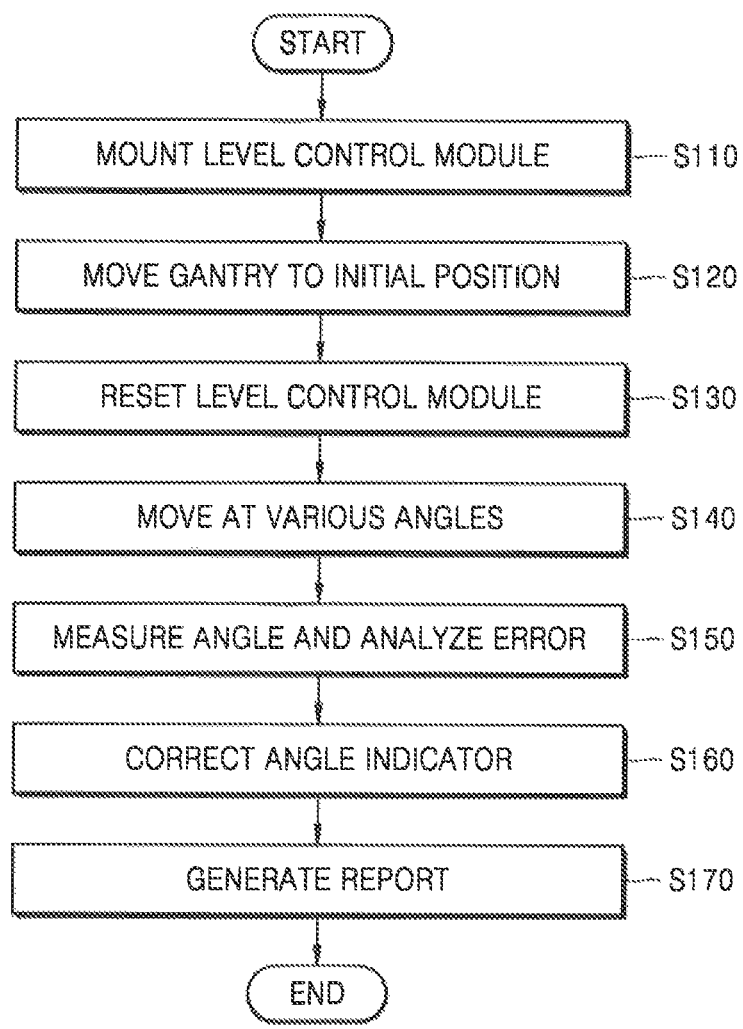
FIG. 4 is a flow diagram illustrating a quality management method for a radiation therapy apparatus according to an embodiment of the inventive concept.

Hereinafter, a quality management method for a radiation therapy apparatus according to an embodiment of the inventive concept will be described. FIG. 4 is a flow diagram illustrating a quality management method for a radiation therapy apparatus according to an embodiment of the inventive concept.

Referring to FIG. 4, a quality management method for a radiation therapy apparatus according to an embodiment of the inventive concept may include: mounting a level control module on the radiation therapy apparatus (operation S110); moving a gantry to an initial position (operation S120); resetting a level control module (operation S130); moving the gantry or a radiation irradiating head at various angles (operation S140); measuring a rotation angle of the gantry or the radiation irradiating head in each state and comparing the measured rotation angle with a rotation angle indicated by an angle indicator of the radiation therapy apparatus to analyze an error (operation S150); reflecting the analyzed error to correct an error of the angle indicator (operation S160); and generating a result report thereof (operation S170).

This will be described below in more detail.

First, the level control module 160 may be mounted on the radiation therapy apparatus 100 (operation S110). In detail, the module mounting guide 131 may be formed to protrude in the direction of irradiation of a radiation from the radiation irradiating head 130, and the level control module 160 may be coupled to the module mounting guide 131.

Thereafter, the gantry may be moved to the initial position (operation S120), and then the horizontality of the electronic level meter 162 may be determined and then the level control module 160 may be reset (operation S130). That is, the current mounting position of the level control module 160 may be set as a reference value.

In this case, when a level error occurs in the electronic level meter 162 of the level control module 160 or in the level control module 160 itself, the level adjuster 163 may be driven to correct the level error of the electronic level meter 162 under the control of the control unit 164.

Thereafter, the gantry 120 or the radiation irradiating head 130 may be moved at various angles (operation 3140), and the rotation angle of the gantry 120 or the radiation irradiating head 130 in each state may be measured and the measured rotation angle may be compared with a rotation angle indicated by an angle indicator (not illustrated) of the radiation therapy apparatus 100 to analyze an error of the angle indicator (operation S150). In this case, when the error is greater than or equal to a predetermined allowable error, this may be displayed on a display unit (not illustrated) of the radiation therapy apparatus 100 to notify an error occurrence to the user.

Thereafter, the analyzed error may be reflected to correct an error of the angle indicator (not illustrated) (operation S160). As a result, the level control module 160 may compare the rotation angle of the gantry 120 or the radiation irradiating head 130 measured by the electronic level meter 162 with a rotation angle indicated by an angle indicator (not illustrated) of the radiation therapy apparatus 100 to automatically correct an error of the angle indicator.

Lastly, the result of the quality management performed by the level control module 160 may be analyzed and the result report thereof may be generated (operation S170). In detail, the report generating unit (not illustrated) may analyze the result of the quality management performed by the level control module 160 and generate a result report thereof. That is, the report generating unit may automatically analyze the quality management performance result and provide the same to the user.

According to the inventive concept described above, since an error of the angle indicator may be calculated and corrected, accurate/precise quality management may be performed on the angle indicator. Also, by using the automated angle correcting device, automated quality management may be performed, and the time, cost, and manpower required for quality management may be reduced. Also, since the quality management results of the respective quality management items performed may be analyzed and the result report thereof may be automatically generated and stored, the quality management history thereof may be systematically stored and analyzed.

The embodiments of the inventive concept described above may be implemented in the form of computer programs that may be executed through various components on a computer, and the computer programs may be recorded in computer-readable recording mediums. Examples of the computer-readable recording mediums may include magnetic recording mediums such as hard disks, floppy disks, and magnetic tapes, optical recording mediums such as CD-ROMs and DVDs, magneto-optical recording mediums such as floptical disks, and hardware devices such as ROMs, RAMs and flash memories that are especially configured to store and execute program commands. Also, the computer-readable recording mediums may include intangible mediums that are implemented in an intangible form transmittable on a network, and may be, for example, mediums that are implemented in the form of software or application and then may be transmitted and distributed over a network.

The computer programs may be those that are especially designed and configured for the inventive concept, or may be those that are known and available to computer programmers skilled in the art. Examples of the computer programs may include machine language codes that may be generated by a compiler, and high-level language codes that may be executed by a computer by using an interpreter.

Particular implementations described herein are merely embodiments, and do not limit the scope of the inventive concept in any way. For the sake of conciseness, descriptions of related art electronic configurations, control systems, software, and other functional aspects of the systems may be omitted. Also, the connection lines or connection members between various elements illustrated in the drawings represent examples of functional connections and/or physical or logical connections between the various elements, and various alternative or additional functional connections, physical connections, or logical connections may be present in practical apparatuses. Also, no element may be essential to the practice of the inventive concept unless the element is specifically described as "essential" or "critical".

Thus, the spirit of the inventive concept is not limited to the above embodiments, and the scope of the inventive concept may include both the following claims and the equivalents thereof.

INDUSTRIAL APPLICABILITY

The embodiments of the inventive concept may be applied to a radiation therapy apparatus and a quality management method for a radiation therapy apparatus, and more particularly, to a radiation therapy apparatus and a quality management method for a radiation therapy apparatus that may automatically measure the accuracy of an angle indicator value of a gantry or a radiation irradiating head and may correct the same.

The invention claimed is:

1. A radiation therapy apparatus on which quality management is performed, the radiation therapy apparatus comprising:
    a body unit;
    a gantry coupled to one side of the body unit and formed to be rotatable in at least one direction with regard to the body unit;
    a radiation irradiating head formed at one side of the gantry to irradiate a radiation; and
    a level control module formed at one side of the radiation irradiating head to measure a rotation angle of the gantry or the radiation irradiating head, compare the measured rotation angle with a rotation angle indicated by an angle indicator of the radiation therapy apparatus, and correct an error of the angle indicator.

2. The radiation therapy apparatus of claim 1, wherein the level control module comprises:
    one or more electronic level meters measuring a rotation angle of the gantry or the radiation irradiating head; and
    a control unit comparing the rotation angle of the gantry or the radiation irradiating head measured by the electronic level meter with a rotation angle indicated by an angle indicator of the radiation therapy apparatus and correcting an error of the angle indicator.

3. The radiation therapy apparatus of claim 2, further comprising a level adjuster formed on at least one side of the electronic level meter to move the electronic level meter in at least one direction and correct a level error of the electronic level meter.

4. The radiation therapy apparatus of claim 2, wherein the control unit notifies an error occurrence to a user when the error of the angle indicator is greater than or equal to a predetermined allowable error.

5. The radiation therapy apparatus of claim 1, wherein a module mounting guide is formed at one side of the radiation irradiating head, and the level control module is mounted on the module mounting guide.

6. The radiation therapy apparatus of claim 1, further comprising a report generating unit generating and providing a result report of the quality management executed by the level control module.

7. The radiation therapy apparatus of claim 1, further comprising a control module calculates a rotation speed of the gantry or the radiation irradiating head and angle information of the gantry or the radiation irradiating head at a particular time by using measurement time information and the rotation angle of the gantry or the radiation irradiating head measured by the level control module, and compares the calculated rotation speed and an angle of the gantry or the radiation irradiating head at a particular time with a rotation speed of the gantry or the radiation irradiating head predetermined at the time of radiation therapy planning and an angle of the gantry or the radiation irradiating head at a particular time.

8. The radiation therapy apparatus of claim 7, wherein the control module generates a predetermined alarm signal when a difference between the calculated rotation speed and the angle of the gantry or the radiation irradiating head at a particular time and the rotation speed of the gantry or the radiation irradiating head predetermined at the time of radiation therapy planning and the angle of the gantry or the radiation irradiating head at a particular time exceeds a predetermined error range.

9. A quality management method for a radiation therapy apparatus, the quality management method comprising:

mounting a level control module on the radiation therapy apparatus;

moving a gantry to an initial position;

measuring a rotation angle of the gantry or a radiation irradiating head at each position by using an electronic level meter while moving the gantry or the radiation irradiating head to one or more positions; and comparing the measured rotation angle with a rotation angle indicated by an angle indicator of the radiation therapy apparatus and correcting an error of the angle indicator.

10. The quality management method of claim 9, further comprising correcting an error of the electronic level meter by a level adjuster formed on at least one side of the electronic level meter to move the electronic level meter in at least one direction.

11. The quality management method of claim 9, further comprising resetting the level control module after the moving of the gantry to the initial position.

12. The quality management method of claim 9, wherein by comparing the measured rotation angle with the rotation angle indicated by the angle indicator of the radiation therapy apparatus, an error occurrence is notified to a user when the error of the angle indicator is greater than or equal to a predetermined allowable error.

13. The quality management method of claim 9, further comprising, after correcting of the error of the angle indicator, generating and providing a result report of the quality management executed by the level control module.

14. A computer program stored in a medium to execute the quality management method of claim 9 by using a computer.

* * * * *